United States Patent [19]

Vallette

[11] 4,307,022
[45] Dec. 22, 1981

[54] PROCESS FOR OBTAINING α,α'-DINITRO ANTHRAQUINONES OF HIGH PURITY

[75] Inventor: Maurice R. J. Vallette, Precy-sur-Oise, France

[73] Assignee: Produits Chimiques Ugine Kuhlmann, Courbevoie, France

[21] Appl. No.: 52,884

[22] Filed: Jun. 28, 1979

[30] Foreign Application Priority Data

Jul. 27, 1978 [FR] France .................................. 78 22217

[51] Int. Cl.$^2$ ............................................. C07C 76/00
[52] U.S. Cl. .................................................... 260/369
[58] Field of Search ........................................ 260/369

[56] References Cited

U.S. PATENT DOCUMENTS 4,042,604 8/1977 Eilingsfeld et al. ................. 260/369
4,053,488 10/1977 Bruenemann et al. .............. 260/369

Primary Examiner—Winston A. Douglas
Assistant Examiner—Raymond K. Covington
Attorney, Agent, or Firm—Beveridge, DeGrandi, Kline & Lunsford

[57] ABSTRACT

The invention relates to a process for obtaining α,α'-dinitro-anthraquinones of high purity from crude mixtures obtained from the dinitration of anthraquinone. Such a mixture is placed in contact with an ester having a boiling point greater than 120° C. derived from a mono- or di-carboxylic acid or phosphoric acid, at a temperature between 20° and 200° C. or more, then, after possible cooling, the insoluble material consisting essentially of the α,α'-dinitro-anthraquinones is separated.

9 Claims, No Drawings

PROCESS FOR OBTAINING α,α'-DINITRO ANTHRAQUINONES OF HIGH PURITY

The present invention relates to a process for the production of α,α'-dinitro-anthraquinones (1,5 and 1,8 isomers) of high purity.

The dinitration of anthraquinone may be effected in sulfuric acid by the action of nitric acid (J. Chem. Soc., 1920, 117, pp. 1001-1004; Hefti, Helv. Chem. Acta, 1931, 14, 1404-1427; French Pat. No. 2,294,162 which corresponds to British Pat. No. 1,523,749 and French Pat. No. 2,151,965 which corresponds to U.S. Pat. No. 3,818,052) or in nitric acid (Boetiger and Pettersen, Annalen, 1881, 166, p. 154 and German patent application Nos. 2,306,611 and 2,351,590) which correspond, respectively, to U.S. Pat. Nos. 3,906,011 and 3,963,762.

During this dinitration and whatever may be the process used, there is formed in addition to the α,α'-dinitro derivatives desired, a more than negligible proportion of α,β, and β,β' derivatives. The 1,5- and 1,8-dinitro-anthraquinones are important intermediate products for the preparation of dyes for natural and synthetic fibers (cf. Color Index Nos. 62,500, 64,500, 65,405, 65,415, 65,425, 69,015, 69,025, and 70,510). In addition, in order to be used, the products obtained from the dinitration must be separated from the 1,6, 1,7, 2,6, and 2,7 isomers which they contain. In order to carry out this separation, various methods have been proposed and used by the prior art:

(a) First, it has been proposed to filter after the nitration in order to profit from the solubility of the α,β and β,β' derivatives in the sulfuric acid (French Pat. Nos. 2,294,162 and 2,151,965). This method, however, has the disadvantage of leading to a not inconsiderable loss of α,α'-dinitro derivatives.

(b) It has also been proposed to subject the dinitration product to an indirect sulfonation by means of an aqueous solution of an alkaline sulfite, the α,β and β,β' derivatives being preferentially attacked (U.S. Pat. No. 2,309,708). Since this reaction is not selective, a considerable loss of α,α' derivatives results.

(c) The separation can also be effected by treating the dinitration mixture with solvents of the hydrocarbon type, ether or acid type in which the α,α' derivatives are substantially insoluble (French Pat. No. 2,313,349 which corresponds to U.S. Pat. No. 4,042,604).

It has now been found that α,α'-dinitro-anthraquinones of high purity can be obtained from mixtures containing, in addition to the α,α' derivatives, up to 50% by weight of α,β and β,β' derivatives and possibly mononitro-anthraquinone and anthraquinone by treatment of such mixture by means of an organic solvent in which the α,α' derivatives are substantially insoluble, when there is used as solvent an ester having a boiling point at atmospheric pressure greater than 120° C., preferably greater than 170° C., derived from a mono- or di-carboxylic acid or phosphoric acid.

The solvents to be used according to the present invention include acetates of which the ester chain comprises 4 to 13 carbon atoms, phosphates of which each ester chain comprises 1 to 7 carbon atoms, benzoates of which the ester chain comprises 1 to 4 carbon atoms, phthalates of which each ester chain comprises 1 to 13 carbon atoms, malonates of which each ester chain comprises 1 to 4 carbon atoms, methyl and ethyl acetylacetates. Preferred solvents are the methyl, ethyl, butyl and tolyl esters of phosphoric acid, methyl or ethyl benzoate, the methyl, butyl, nonyl and tridecyl esters of phthalic acid, the methyl and ethyl esters of malonic acid, ethyl acetylacetate, n.butyl, octyl, nonyl, cyclohexyl or p-totyl acetate and mixtures of these solvents. For technical reasons, dialkyl phthalates of which each alkyl radical, linear or branched, contains 1 to 13 carbon atoms, are preferably used, and for economic reasons, the phthalates with branched chains such as those derived from an alcohol obtained by the oxo process are preferred above all.

The mixture to be purified may be provided from the dinitration of anthraquinone or by the nitration of 1-nitro-anthraquinone with nitric acid, possibly in the presence of sulfuric acid. It also relates to mixtures produced synthetically.

In order to effect the process according to the invention, the mixture to be purified is treated with the solvent at a temperature between 20° and 200° C. or higher, preferably between 50° and 200° C.; then, after possible cooling, the insoluble portion consisting essentially of α,α' derivatives is separated by the usual methods, for example by filtration.

It is evident that unless working under pressure, the temperature of the treatment must be less than the boiling point of the solvent used. The mixture to be purified may be introduced into the solvent previously heated to the selected temperature for the treatment; the mixture to be purified may also be introduced into cold solvent, which is then heated to the selected temperature. The time of contact between the solvent or solvents and the mixture to be purified may vary between 30 minutes and 15 hours.

In general, the solvent is used in an amount by weight between 2 and 12 times, preferably between 2 and 6 times, that of the mixture to be purified considered as the dry state. This amount is preferably inversely proportional to the temperature of filtration.

Extending the time of contact beyond 15 hours or using an amount of solvent more than 12 times the dry weight of the mixture to be purified does not cause any inconvenience nor does it adversely affect the purification, but is also of no particular advantage.

Instead of starting from a mixture to be purified in the dry state, a press cake from the nitration may be directly used and a dehydration effected by distillation with the solvent used.

The yield from the operation may be improved by recycling the filtrate.

The solvent remaining in the cake after filtration may be removed by washing the latter with other solvents such as methanol, ethanol and tert.-butanol.

The following examples, in which all parts and percentages are by weight, illustrate the invention without it being limited thereto.

EXAMPLE 1

75 Parts of a mixture of dinitro-anthraquinones having the following composition:

| | |
|---|---|
| 1,5-dinitro-anthraquinone | 41.7% |
| 1,8-dinitro-anthraquinone | 37.8% |
| 1,6- and 1,7-dinitro-anthraquinones | 17.5% |
| 2,6- and 2,7-dinitro-anthraquinones, 1-nitro-anthraquinone and anthraquinone | 3.0% | are placed with stirring in contact with 300 parts of dinonyl phthalate. The mixture is heated to 180° C. and this temperature is maintained for 2 hours; then the mixture is allowed to cool to 170° C. and maintained at this temperature for 30 minutes. It is then filtered on fritted glass previously heated to 170° C., drained and the cake washed with methanol and dried at about 60° C. until its weight is constant. 53 Parts of a mixture of 1,5- and 1,8-dinitro-anthraquinones at 96.9% purity (51.8% of 1,5-isomer and 45.1% of 1,8-isomer) are obtained, that is, a theoretical yield of 86.1%.

EXAMPLE 2

Example 1 is repeated with the exception that the dinonyl phthalate is replaced by dioctyl phthalate. An identical yield and purity are obtained.

EXAMPLE 3

Example 1 is repeated with the exception that 225 parts of dinonyl phthalate are used. 56 Parts of a mixture of 1,5-dinitro- and 1,8-dinitro-anthraquinones at 95.9% purity (51% of 1,5-isomer and 44.9% of 1,8-isomer) are obtained, that is a theoretical yield of 90%.

EXAMPLE 4

Example 3 is repeated with the exception that it is carried out with dioctyl phthalate. The same yield with the same degree of purity is obtained.

EXAMPLE 5

The operation of Example 1 is repeated starting from a mixture of dinitro-anthraquinones having the following composition:

| | |
|---|---|
| 1,5-dinitro-anthraquinone | 51.6% |
| 1,8-dinitro-anthraquinone | 39.6% |
| 1,6- and 1,7-dinitro-anthraquinones | 8.3% |
| 2,6- and 2,7-dinitro-anthraquinones, 1-nitro-anthraquinone and anthraquinone | 0.5% |

65.1 Parts of 1,5-dinitro and 1,8-dinitro-anthraquinones at 97.6% purity (56.9% of isomer 1,5 and 40.7% of isomer 1,8), are obtained that is, a theoretical yield of 92.8%.

EXAMPLE 6

Example 1 is repeated with the exception that the dinonyl phthalate is replaced by dimethyl phthalate and the starting mixture of dinitroanthraquinones has the following composition:

| | |
|---|---|
| 1,5-dinitro-anthraquinone | 30.2% |
| 1,8-dinitro-anthraquinone | 60.6% |
| 1,6- and 1,7-dinitro-anthraquinones | 7.0% |
| 2,6- and 2,7-dinitro-anthraquinones, 1-nitro-anthraquinone and anthraquinone | 2.2% |

31.5 Parts of a mixture of 1,5- and 1,8-dinitro-anthraquinones at 99.5% purity (54.5% of isomer 1,5 and 45% of isomer 1,8) are obtained, that is, a theoretical yield of 46%.

EXAMPLE 7

Example 1 is repeated with the exception that the dinonyl phthalate is replaced by dimethyl phthatate and one cools to 70° C. and filters at this temperature. 51 Parts of a mixture of 1,5- and 1,8-dinitro-anthraquinones are obtained of 98.2% purity (54% of isomer 1,5 and 44.2% of isomer 1,8), that is, a theoretical yield of 84%.

EXAMPLE 8

Example 1 is repeated with the exception that the dinonyl phthalate is replaced by diethyl phthalate. 31.8 Parts are obtained of a mixture of 1,5- and 1,8-dinitro-anthraquinones at 98.2% purity (80.4% of isomer 1,5 and 17.8% of isomer 1,8), that is, a theoretical yield of 52.4%.

EXAMPLE 9

Example 1 is repeated with the exception that the dinonyl phthalate is replaced by diethyl phthalate and one cools to 20° C. and filters at this temperature. 61.5 Parts of a mixture of 1,5- and 1,8-dinitro-anthraquinones are obtained of 90.4% purity (47.1% of isomer 1,5 and 43.3% of isomer 1,8).

EXAMPLE 10

Example 1 is repeated with the exception that the dinonyl phthalate is replaced by dibutyl phthalate. 45.7 Parts are obtained of a mixture of 1,5- and 1,8-dinitro-anthraquinones at 98.2% purity (57.4% of isomer 1,5 and 40.8% of isomer 1,8), that is, a theoretical yield of 75.2%.

EXAMPLE 11

Example 1 is repeated using 225 parts of dibutyl phthalate instead of 300 parts of dinonyl phthalate. 47.8 Parts are obtained of a mixture of 1,5- and 1,8-dinitro-anthraquinones at 96.9% purity (56.8% isomer 1,5 and 40.1% isomer 1,8), that is, a theoretical yield of 77.6%.

EXAMPLE 12

Example 5 is repeated with the exception that the dinonyl phthalate is replaced by diethyl phthalate. 49.2 Parts of a mixture of 1,5- and 1,8-dinitro-anthraquinones are obtained of 99% purity (72.6% of 1,5 isomer and 26.4% of 1,8 isomer), that is, a theoretical yield of 71.2%.

EXAMPLE 13

Example 5 is repeated with the exception that the dinonyl phthalate is replaced by dibutyl phthalate. 57.8 Parts are obtained of a mixture of 1,5- and 1,8-dinitro-anthraquinones at 97.4% purity (60.8% of isomer 1,5 and 36.6% of isomer 1,8), that is, a theoretical yield of 82.2%.

EXAMPLE 14

Example 1 is repeated with the exception that the dinonyl phthalate is replaced by a mixture of dialkyl phthalates of $C_7$ to $C_{11}$. 53.4 Parts are obtained of a mixture of 1,5- and 1,8-dinitro-anthraquinones at 95.7% purity (50.5% of isomer 1,5 and 45.2% of isomer 1,8), that is, a theoretical yield of 85.6%.

EXAMPLE 15

Example 1 is repeated with the exception that the dinonyl phthalate is replaced by ditridecyl phthalate. 53.7 Parts are obtained of a mixture of 1,5- and 1,8-dinitro-anthraquinones at 94.7% purity (52.2% of 1,5-isomer and 42.5% of 1,8-isomer), that is, a theoretical yield of 85.2%.

EXAMPLE 16

Example 1 is repeated with the exception that the dinonyl phthalate is replaced by ethyl benzoate. 32.8 Parts are obtained of a mixture of 1,5- and 1,8-dinitroanthraquinones at 98.7% purity (80.1% of isomer 1,5 and 18.6% of isomer 1,8), that is, a theoretical yield of 54.3%.

EXAMPLE 17

Example 5 is repeated with the exception that the dinonyl phthalate is replaced by tri-ortho-tolyl phosphate. 59.6 Parts are obtained of a mixture of 1,5- and 1,8-dinitro-anthraquinones at 98.7% purity (63.5% of isomer 1,5 and 35.2% of isomer 1,8), that is, a theoretical yield of 86%.

EXAMPLE 18

Example 1 is repeated with the exception that the dinonyl phthalate is replaced by 150 parts of dimethyl phthalate. 37.2 Parts are obtained of a mixture of 1,5- and 1,8-dinitro-anthraquinones at 98.3% purity (72% of isomer 1,5 and 26.3% of isomer 1,8), that is, a theoretical yield of 61%.

EXAMPLE 19

Example 1 is repeated with the exception that the dinonyl phthalate is replaced by 225 parts of dimethyl phthalate and one cools to 50° C. and filters at this temperature. 56.2 Parts are obtained of a mixture of 1,5- and 1,8-dinitro-anthraquinones at 94.7% purity (52.5% of isomer 1,5 and 42.2% of isomer 1,8), that is, a theoretical yield of 89.2%.

EXAMPLE 20

305 Parts of dinonyl phthalate are placed in contact with stirring with 260 parts of a press cake obtained from the dinitration of anthraquinone and containing 75 parts of a mixture of dinitro-anthraquinones having the same percentage composition as in Example 1. By heating up to 180° C. and maintaining this temperature for two hours, the water (185 parts) is removed by distillation at the same time as 5 parts of dinonyl phthalate. The mixture is then cooled to 170° C., maintained at this temperature for 30 minutes and the procedure completed as in Example 1.

53.8 Parts are obtained of a mixture of 1,5- and 1,8-dinitro-anthraquinones at 93.9% purity (52.8% of isomer 1,5- and 41.1% of isomer 1,8), that is, a theoretical yield of 84.7%.

EXAMPLE 21

Example 1 is repeated with the exception that the dinonyl phthalate is replaced by the same quantity of ethyl acetylacetate. 47 Parts are obtained of a mixture of 1,5- and 1,8-dinitro-anthraquinones at 97% purity (55.5% of isomer 1,5 and 41.5% of isomer 1,8), that is, a theoretical yield of 76.5%.

EXAMPLE 22

Example 1 is repeated with the exception that the dinonyl phthalate is replaced by the same amount of diethyl malonate. 51.5 Parts are obtained of a mixture of 1,5- and 1,8-dinitro-anthraquinones at 94.2% purity (50.2% of isomer 1,5 and 44% of isomer 1,8), that is, a theoretical yield of 81.3%.

EXAMPLE 23

Example 1 is repeated with the exception that the dinonyl phthalate is replaced by a mixture of 225 parts of dimethyl phthalate and 75 parts of diethyl phthalate and that one cools to 70° C. and filters at this temperature. 50.7 Parts are obtained of a mixture of 1,5- and 1,8-dinitro-anthraquinones at 97.9% purity (52.9% of isomer 1,5 and 45% of isomer 1,8), that is, a theoretical yield of 83.2%.

EXAMPLE 24

Example 1 is repeated with the exception that the dinonyl phthalate is replaced by a mixture of 225 parts of dimethyl phthalate and 75 parts of dinonyl phthalate and that one cools to 70° C. and filters at this temperature. One obtains 55.3 parts of a mixture of 1,5- and 1,8-dinitro-anthraquinones at 91.7% purity (50.4% of isomer 1,5 and 41.3% of isomer 1,8), that is, a theoretical yield of 85%.

In the examples in which long chain ($C_7$ to $C_{13}$) dialkyl phthalates are used, results are obtained approximately equivalent whether the chain is linear or branched.

EXAMPLE 25

The operation is as in Example 1 with the exception that the dinonyl phthalate is replaced by the same amount of n.nonyl acetate and one starts from a mixture of dinitroanthraquinones having the following composition:

| | |
|---|---|
| 1,5-dinitro-anthraquinone | 41.3% |
| 1,8-dinitro-anthraquinone | 35.9% |
| 1,6- and 1,7-dinitro-anthraquinones | 20.6% |
| 2,6- and 2,7-dinitro-anthraquinones, 1-nitro-anthraquinone and anthraquinone | 2.2% |

56.5 Parts of a mixture of 1,5- and 1,8-dinitro-anthraquinones at 94.6% purity (47.9% of isomer 1,5 and 46.7% of isomer 1,8) are obtained, that is, a theoretical yield of 92.3%.

EXAMPLE 26

Example 25 is repeated with the exception that the n.nonyl acetate is replaced by n.octyl acetate. 56.8 Parts of a mixture of 1,5- and 1,8-dinitro-anthraquinones at 92.9% purity (47.4% of isomer 1,5 and 45.5% of isomer 1,8) are obtained, that is, a theoretical yield of 91.1%.

EXAMPLE 27

Example 25 is repeated with the exception that the n.nonyl acetate is replaced by cyclohexyl acetate. 54.4 Parts of a mixture of 1,5- and 1,8-dinitro-anthraquinones at 94.9% purity (51.6% of isomer 1,5 and 43.3% of isomer 1,8) are obtained, that is, a theoretical yield of 89.2%.

EXAMPLE 28

Example 25 is repeated with the exception that the n.nonyl acetate is replaced by p-tolyl acetate. 25.1 Parts of a mixture is 1,5- and 1,8-dinitro-anthraquinones at 99.5% purity (89.5% of isomer 1,5 and 10% of isomer 1,8) are obtained, that is, a theoretical yield of 43.1%.

EXAMPLE 29

800 Parts of n.butyl acetate are placed in contact with stirring with 75 parts of the same mixture of dinitro-anthraquinones used in Example 25. This mixture is heated to 120° C. and this temperature is maintained for 2 hours, then the mixture is filtered at 120° C. on fritted glass previously heated, drained, and the cake washed with methanol and dried at about 60° C. until its weight is constant. 54 Parts of a mixture of 1,5- and 1,8-dinitroanthraquinones at 92.4% purity (47.2% of isomer 1,5 and 45.2% of isomer 1,8) are obtained, that is, a theoretical yield of 86.1%.

What is claimed is:

1. In a process for obtaining $\alpha,\alpha'$-dinitro-anthraquinones of high purity from a mixture containing, in addition to the $\alpha,\alpha'$ derivatives, up to 50% by weight of a member selected from the group consisting of $\alpha,\beta$ and $\beta,\beta'$ derivatives and mixtures thereof with mononitro-anthraquinone and anthraquinone, by treatment of said mixture with an organic solvent in which the $\alpha,\alpha'$ derivatives are substantially insoluble, the improvement which comprises using as solvent an ester of a mono- or di-carboxylic acid or phosphoric acid, the boiling point of said ester at atmospheric pressure being greater than 120° C.

2. The process according to claim 1 in which the mixture to be purified is put in contact for at least 30 minutes with at least 2 times the dry weight thereof of the solvent at a temperature between 20° and 200° C., said temperature being less than that of the boiling point of the solvent used, then, after possible cooling, the insoluble material consisting essentially of the $\alpha,\alpha'$-dinitro-anthraquinones is separated.

3. The process according to claims 1 or 2 in which there is used as solvent an acetate of which the ester chain contains 4 to 13 carbon atoms, a phosphate of which each ester chain contains 1 to 7 carbon atoms, a benzoate of which the ester chain contains 1 to 4 carbon atoms, a phthalate of which each ester chain contains 1 to 13 carbon atoms, a malonate of which each ester chain contains 1 to 4 carbon atoms, methyl or ethyl acetylacetate or a mixture of said solvents.

4. The process according to claims 1 or 2 in which the solvent is a dialkyl phthalate of which each alkyl radical may be linear or branched and contains 1 to 13 carbon atoms.

5. The process according to claims 1 or 2 in which the solvent is a phthalate of an alcohol obtained by the oxo process.

6. The process according to claim 5 in which the mixture to be purified is in the form of a press cake and the water therein is removed by distillation in the presence of the solvent.

7. The process according to claim 4 in which the mixture to be purified is in the form of a press cake and the water therein is removed by distillation in the presence of the solvent.

8. The process according to claim 3 in which the mixture to be purified is in the form of a press cake and the water therein is removed by distillation in the presence of the solvent.

9. The process according to claims 1 or 2 in which the mixture to be purified is in the form of a press cake and the water therein is removed by distillation in the presence of the solvent.

* * * * *